United States Patent [19]

Temple

[11] 4,297,032

[45] Oct. 27, 1981

[54] DARK FIELD SURFACE INSPECTION ILLUMINATION TECHNIQUE

[75] Inventor: Paul A. Temple, Ridgecrest, Calif.

[73] Assignee: The United States of America as represented by the Secretary of the Navy, Washington, D.C.

[21] Appl. No.: 121,625

[22] Filed: Feb. 14, 1980

[51] Int. Cl.³ ............... G01N 21/21; G01N 21/47; G01N 21/88; G01J 4/00

[52] U.S. Cl. ............................. 356/366; 356/239; 356/337

[58] Field of Search ................. 356/364–370, 356/337, 239–240, 237; 250/225, 572

[56] References Cited

U.S. PATENT DOCUMENTS

| | | |
|---|---|---|
| 552,641 | 1/1896 | Hoskins . |
| 3,361,025 | 12/1961 | Gaffard . |
| 3,475,615 | 11/1967 | Samuel . |
| 3,533,704 | 10/1970 | Krenmayr ............... 356/240 |
| 3,652,863 | 5/1970 | Gaskell et al. . |
| 3,939,350 | 2/1976 | Kronick et al. .......... 356/36 |
| 3,985,454 | 3/1976 | Fletcher et al. ......... 356/237 |
| 3,988,068 | 12/1976 | Sprague .................. 356/124 |
| 4,181,441 | 1/1980 | Noller .................... 356/436 |

FOREIGN PATENT DOCUMENTS

1172059 6/1964 Fed. Rep. of Germany ...... 356/368

OTHER PUBLICATIONS

Holm et al., "Thin-Film Absorption Coefficients by Attenuated-Total-Reflection Spectroscopy", App. Optics, 2-1978, pp. 394–403.
Azzam, R. M. A., "Use of a Light Beam to Probe the Cell Surface in Vitro", Surface Science, 6-1976, pp. 126–133.
Mattson et al., "Identification of Surface Functional Groups on Active Carbon by Infrared Reflection Spectrophotometric", Analytic Chem. 2-1969, pp. 355–358.

*Primary Examiner*—William H. Punter
*Attorney, Agent, or Firm*—R. S. Sciascia; W. Thom Skeer; Kenneth G. Pritchard

[57] ABSTRACT

A method and apparatus for observing imperfections on the surface of and imbedded in an optical sample using a dark field technique. Linearally polarized laser light is entered by a prism-fluid index matching method which causes internal reflection at the critical angle. The internally reflected beam then coherently combines with the incident beam in the vicinity of the sample surface. This results in a standing wave pattern which can be adjusted by changing the laser wavelength, the angle of incidence or polarization to selectively illuminate variously regions at and below the surface. One polarization will have maximum intensity at the surface level while the alternate polarization will have a null at the surface level. Defects within the optical sample scatter light such that it does not reach the surface at an angle equal to or greater than the critical angle. This light is emitted from the sample surface and appears as a pattern of bright spots on a dark background. A viewing piece is used to systematically scan the surface of the sample. Using the above standing wave pattern, it is possible to illuminate the surface with a maximum intensity, to learn the position of optical sample imperfections and to determine the sizes of those imperfections. Placing a drop of oil on the surface of the sample removes surface irregularities as a source of scattered light. The oil drop also permits greater control of standing wave patterns within the sample.

17 Claims, 5 Drawing Figures

DARK FIELD SURFACE INSPECTION ILLUMINATION TECHNIQUE

BACKGROUND OF THE INVENTION

1. Field of the Invention

This invention pertains to methods of evaluating optical scratches and other damage to coated and uncoated optical samples. In particular, the present invention pertains to an apparatus and method permitting detailed scanning throughout the depth of an optical sample to identify the exact location of imperfections within the sample.

2. Description of the Prior Art

Previous techniques for evaluating the quality of optical samples have included:
 a. Straight through or bright field technique which does not discern subtle contrasts,
 b. Normarski or back reflection technique which does not look at the subsurface but only the surface scratches, and
 c. the dark field or grazing angle reflection technique. None of these techniques provide information on the size of small imperfections beneath 500 angstroms or the position of such imperfections.

Previous internal microscopy has been limited to thin plates with beveled edges. This technique creates numerous reflections within the plate. Since each reflection must lose some light, this method is limited to loss spectroscopy.

SUMMARY OF THE INVENTION

A well collimated beam of light such as linerally polarized light from a laser is transmitted into a prism. When the light reaches the exit side of the prism, it encounters a layer of index matching fluid which it transmits through and an optical sample which it continues to transmit through. The optical sample, index matching fluid and prism are all of similar index of refraction to permit continued transmittance of the light. The purpose of the arrangement is to permit light to be present within the optical sample at or greater than the critical angle whenever it reaches the surface. Upon reaching the surface of the optical sample the light undergoes total internal reflection off of the surface because it is at the critical angle and is transmitted back through the sample, index matching fluid and prism. The light exits from the prism.

For an optical sample without any imperfections, viewing the surface of the sample above the area of internal reflection will show a dark field. However, any irregularities within the sample or on the surface of the sample will scatter the light. Some of this light will be scattered towards the surface of the sample at a non-critical angle. This light will emerge and be seen as a bright feature. The polarization of the light is dependent on the nature of the scatterers. Observation of such features throughout the optical sample permits a detailed analysis of the imperfections of the sample. A viewing device ideal for such observations is a microscope. A polarization analyzer can be placed between the microscope and the sample to determine the state of polarization of the scattered light. The sample can be moved over the prism to permit all areas of the sample to be observed.

The linearly polarized light within the optical sample will establish a standing wave pattern. As described herein, the standing wave pattern properties occur for monochromatic polarized light. This pattern will have peaks and nulls within the depth of the sample. If a very small imperfection occurs at a point where a null occurs, it will not be observed. For a small imperfection to be observed, it will have to be illuminated with the peak of a standing wave pattern. For larger imperfections, the site which is positioned at a null will remain visible because it is larger than the null. The change in visibility is used to determine the size of the imperfection. The peaks and nulls within the sample can be alternated by changing the polarization of the light present. Such polarization changes will also give an indication of the depth of any imperfection within the sample. A further refinement of identification of imperfections can be obtained by coating the surface of the optical sample with a drop of oil. This oil will again have an index of refraction similar to the sample. The oil will fill all scratches on the surface of the sample and effectively eliminate them. Thus a second viewing of the sample will only show imperfections which are imbedded in the sample and omit surface scratches.

An alternate technique is to tune the monochromatic light to different monochromatic wavelengths and thus change the standing wave pattern. As the peaks and nulls are shifted by the changing wavelength, features will appear and disappear as the peaks and nulls change depth within the sample. An alternate way of using the same effect is to change the angle of orientation of the light within a sample to angles greater than the critical angle. This changes the distribution of the peaks and nulls of the standing wave by broadening them over a larger scale. This last technique coupled with the use of an oil drop on the surface will permit peaks and nulls to be brought up through the surface of the optical sample itself.

DESCRIPTION OF THE PREFERRED EMBODIMENT

Figure 1:
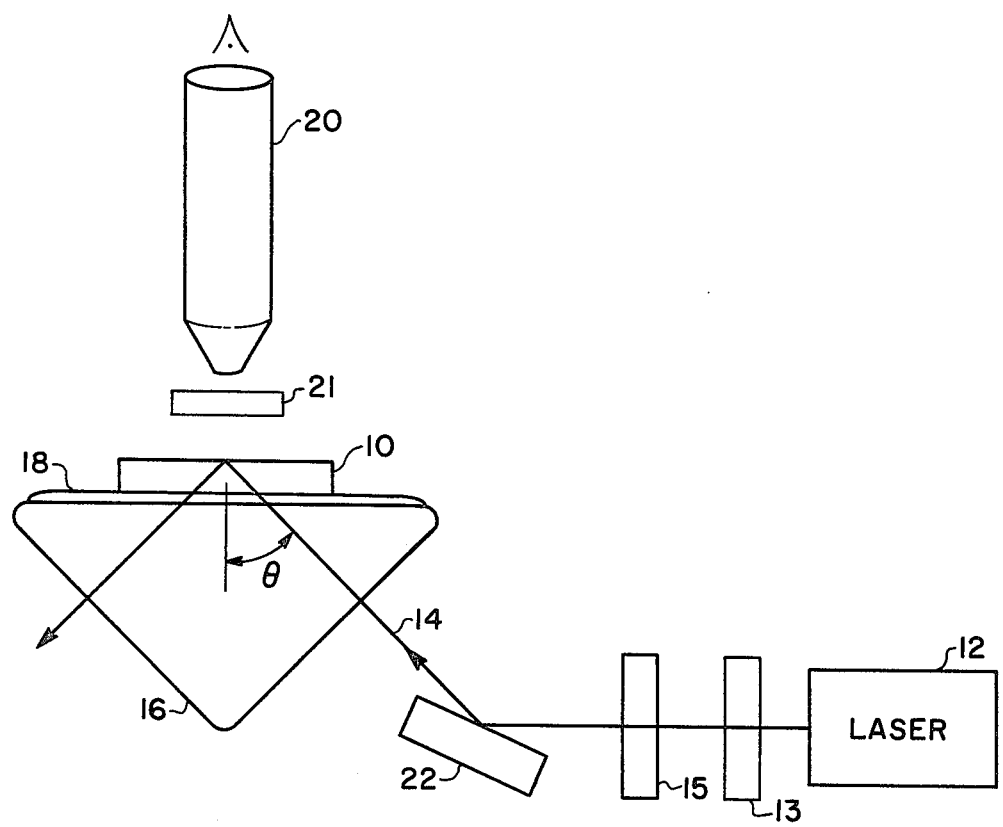
FIG. 1 is a diagram of a preferred embodiment for the present invention.

FIG. 1 is an embodiment of the present invention which permits surface irregularities of an optical sample 10 as well as imbedded imperfections in optical sample 10 to be viewed by a dark field technique. The general term defects will refer to all possible observed features including imbedded imperfections, surface scratches and contaminents on the surface. Linearlly polarized monochromatic light from a tunable laser 12 is transmitted along optical path 14. For unpolarized light, path 14 can first pass through a polarizer 13. For a polarized source the beam passes through a Babinet-Soleil compensator 15 which rotates the polarization of the light to a predetermined orientation. The beam of light travelling along optical path 14 then reflects off a mirror 22 and enters a prism 16 which has an index of refraction similar to or identical to optical sample 10. Mirror 22 is a steering device that controls the angle $\theta$ shown in FIG. 1. The use of prism 16 permits the light to enter the prism at a non-critical angle. Once the light is transmitted within prism 16, it will encounter the second surface of the prism. To avoid reflection, a layer of index matching fluid 18 is used to coat one surface of prism 16. The thickness of fluid 18 in FIG. 1 is greatly exaggerated for purposes of example. Light travelling along path 14 now continues into index matching fluid 18. On top of index matching fluid 18, optical sample 10 is placed. Optical sample 10 now has light enter it along path 14. The light within optical sample 10 now encounters the upper surface of sample 10 at an angle which is equal to or greater than the critical angle for total internal reflection. If optical sample 10 has no defects in the illuminated area, a person observing the surface area of optical sample 10 from an observation point 20, which can be a microscope, will see nothing. As shown in FIG. 1, observation point 20 views light exiting normal to the surface of optical sample 10. Index matching fluid 18 also serves as a lubricant to permit movement of sample 10 over prism 16 so all of sample 10 can be observed except for a narrow edge about sample 10. An alternate method of viewing all of sample 10 is to move prism 16. Plane surfaces on the bottom of sample 10 and the top of prism 16 are exemplary. Matching contoured surfaces can be used to study lenses and such.

The viewing of no light gives rise to the title dark field. However, if there are surface scratches or imbedded imperfections, light travelling along path 14 will undergo scattering. Some of the scattered light will be directed upwards out of optical surface 10 and encounter the upper surface at less than the critical angle. This scattered light will be emitted from optical surface 10 and scratches and imperfections will show up as a pattern of bright spots against a dark background. A polarization analyser 21 can be placed between sample 10 and observation point 20 to determine the state of polarization of the scattered light.

Surface scratches can be separately identified from imbedded imperfections by raising the upper surface of optical sample 10 with a coat of material of matching index of refraction. The coating will provide a smooth surface on optical sample 10. The coating fills in all surface scratches and raises the surface where total internal reflection occurs. Any surface scratches previously viewed will now be eliminated and the only imperfections seen will be those imbedded in the sample. Care should be taken that the coating is a uniform thickness and that it does not contain dust or other impurities. Impurities would appear as new bright spots. The coating can be a drop of oil or any other suitable material deposited on the sample. On a known optical sample, this method can be used to view impurities such as microbes on the surface of the sample or suspended within the coating.

Figure 2:
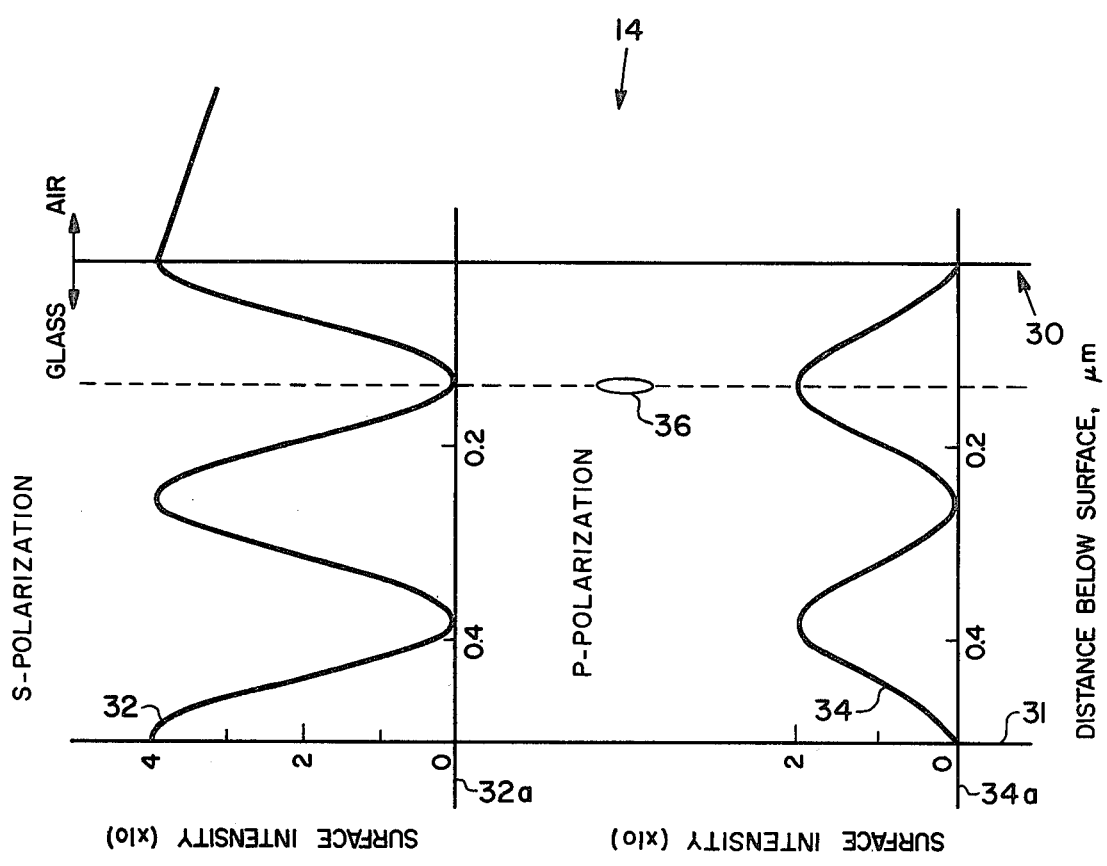
FIG. 2 is a diagram of the change in peaks and nulls obtained by changing polarity.

FIG. 2 shows the standing wave patterns of linearlly polarized light near the surface of optical sample 10. Line 30 represents the upper surface of optical sample 10. Line 31 represents a level a few microns beneath line 30. The standing wave pattern exits in the region beneath the surface of optical sample 10 where the incoming beam and reflected beam overlap. White light obviously cannot be used because the coherence length for interference is so short. In contrast, monochromatic light has large coherence lengths which provide the necessary depth to search for small imbedded imperfections. While this region is small compared to the depth of the sample, it contains thousands of standing waves. Standing wave pattern 32 and standing wave pattern 34 are compared to the reference level of light itensity, lines 32a and 34a. Wave patterns 32 and 34 represent "s" and "p" polarization respectively. Peaks and nulls of the standing wave patterns are alternated at a given wave length. One polarization, curve 32, has a maximum intensity at the surface of the sample while the alternate polarization 34 has a null at the surface of the sample. If the incident light has an intensity of $I_o$ and it enters the sample for curve 32, the surface intensity will be $4I_o$ and for curve 34 the peaks will be approximately $2I_o$. Thus, it can be seen that only one component of polarization illuminates small imperfections when viewed from directly above. As a result, a small imperfection, such as 36, will not be seen for polarization 32 but will be brightly illuminated for polarization 34. The result of this change in information by changing the polarization is to provide a way to measure the depth of imperfection 36 within the optical sample. For the standing wave pattern shown, for any given polarization, there will be several possible depths for which imperfection 36 would appear. For polarization 32, there are several possible depths at which an imperfection could be illuminated. To identify which of the locations is the correct one, the laser light coming along path 14 can be tuned to cause the standing waves to vary their nulls and peaks. As the standing wavelength increases, the possible location of imperfection 36 will consist of a different set of values. Location of imperfections can be identified this way. In a real sample, several different wavelengths will have to be used to isolate the impurity. Also as previously discussed, surface irregularities or scratches can be eliminated as a possible area of consideration by using a drop of oil on the surface.

Another way of identifying the depth of the imperfections within the optical sample is to change the incident angle to one greater than the critical angle. When this is done, the standing wave pattern expands. By using the same polarization, but expanding the peaks and nulls, imperfections can effectively be tuned in and out of a peak and null for a given polarization. This can be done in FIG. 1 by mirror 22 which can be used to deflect the beam to angles greater than the critical angle.

Lastly, combining two of these methods, placing an oil drop on the upper most surface and then changing the incident angle permits the upper most null to go all the way to the surface of the oil drop. Without the oil drop, the upper most null shown for polarization 34 can never get closer to the surface and only expand away from it. With the oil drop, the upper most null can actually be shifted above the optical sample itself and into the layer provided by the oil drop.

Figure 3:
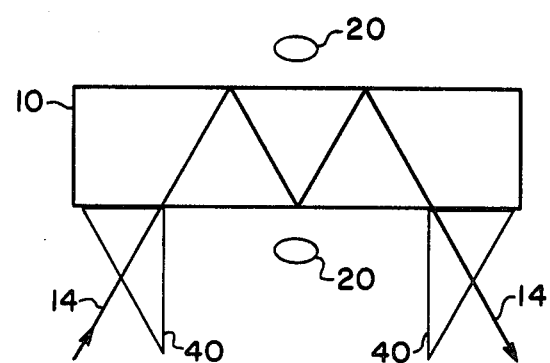
FIGS. 3 and 4 show alternate methods of coupling light into an optical sample.

FIG. 3 shows an alternate way of coupling light into optical sample 10. Two prisms 40 are used to couple light in and out as described previously. The difference is that now the bottom of optical sample 10 is not obstructed. Light travelling along optical path 14 now undergoes several total internal reflections. The advantage of the FIG. 3 arrangement is that see-through laser evaluation of a sample can be made at various stages of a test lifetime without repeated disassembly for testing. For each internal reflection point, light will be scattered both up and down. Thus, two possible observation points 20 are possible.

Figure 4:
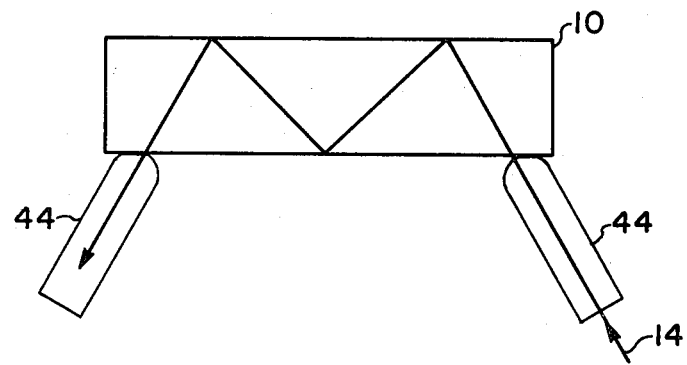

FIG. 4 shows a dry technique for coupling light into optical sample 10. A soft plastic rounded rod 44 is slightly deformed by contact with optical sample 10.

This permits controlled access and egress points for light along optical path 14.

Figure 5:
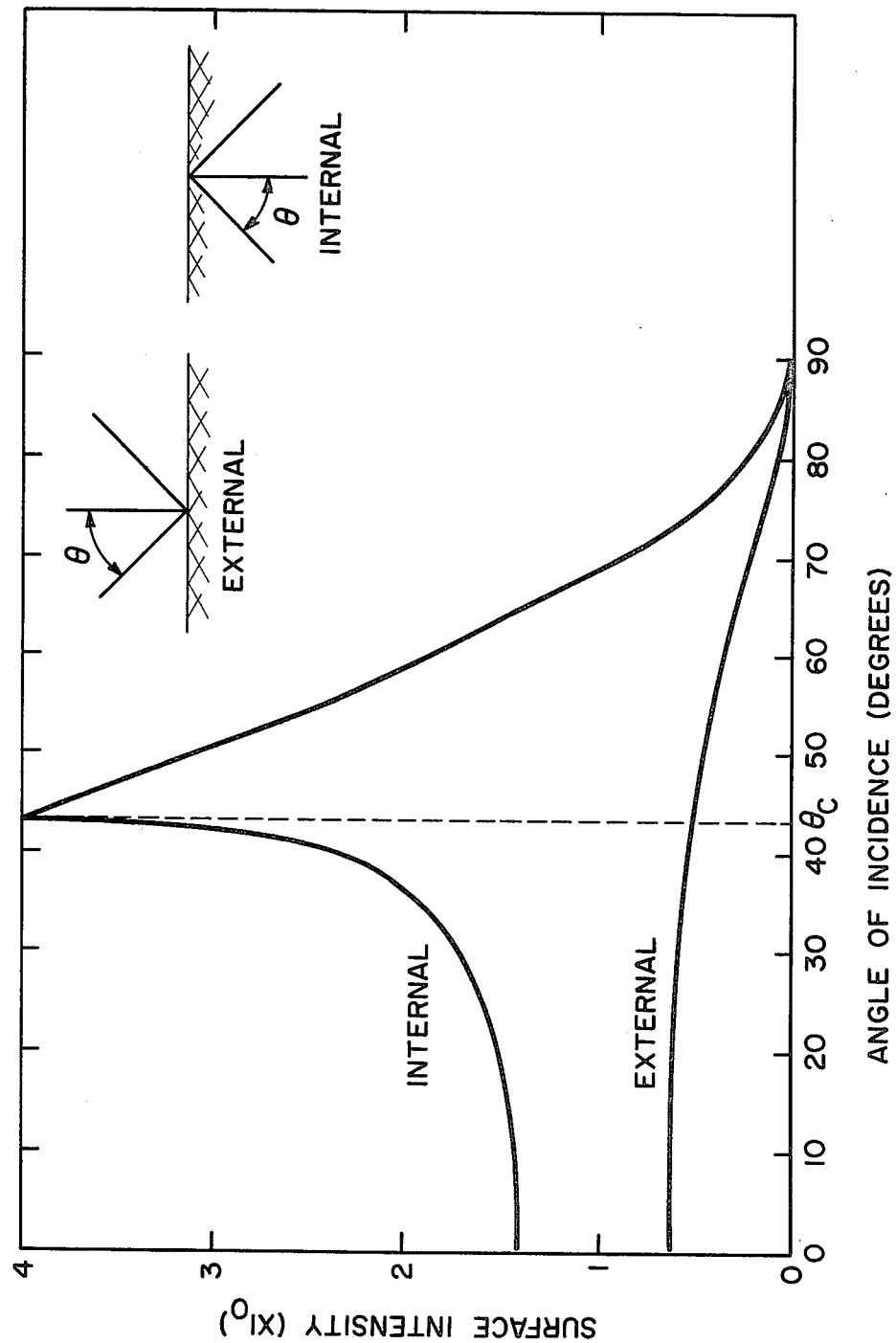
FIG. 5 is a graph of surface light intensity vs. angle of incidence for external and internal illumination of an optical sample.

FIG. 5 is a graph which shows the difference in the surface intensity of light, $I_o$, vs angle of incidence for internal and external reflection. The critical angle is $\theta_c$. In this graph an index of refraction, n=1.47, for fused quartz has been used. The polarization shown is S-polarization which corresponds to curve 32 in FIG. 2. The amount of light available to illuminate defects is far greater for internal reflection at or near the critical angle, $\theta_c$. In addition, the external light does not create a useful standing wave pattern as internal light does.

The above invention can be used with many optical areas and particularly has been used with visible light for glass optics. However, it is clear to those skilled in the art that this method will be applicable to a wide range of optical areas.

What is claimed is:

1. A surface inspection method for finding defects contained in or on an optical sample comprising the steps of:

coating one side of a prism whose index of refraction is similar to said optical sample with an index matching fluid;

placing said optical sample on said fluid coated side;

establishing an observation point above said optical sample to view the surface at a normal angle;

directing a beam of monochromatic polarized light into said prism such that said beam reflects off of the upper surface of said optical sample at the critical angle beneath said observation point so as to create a standing wave pattern which scatters light off of imperfections smaller than the wavelength of said standing waves except when said imperfections are located at null points of said standing waves;

varying the standing wave pattern so that the null points of said standing waves occur at different depths within the optical sample, the imperfections appear and disappear as null points pass through it;

comparing the possible depths at which the imperfections appear for a plurality of different standing wave patterns to uniquely identify the depth in the sample of each imperfection; and moving said optical sample so that all areas of said optical sample are viewed from said observation point to observe said scattered light which has been scattered toward said upper surface at less than the critical angle.

2. A surface inspection method for finding defects contained in or on an optical sample as described in claim 1 where the standing wave pattern is varied by:

changing the polarization of said polarized light such that the standing wave patterns within said optical sample vary the locations of peaks and nulls to locate the position of imperfections with said optical sample.

3. A surface inspection method for finding defects contained in or on an optical sample as described in either of claims 1 or 2 further comprising the step of:

altering the incident angle of said beam of polarized light to one greater than the critical angle such that the standing wave pattern expands to show imbedded imperfections at different depths in said optical sample.

4. An apparatus for locating defects in or on an optical sample comprising:

a source of monochromatic light for emitting a beam of polarized light, said polarization capable of being changed, along an optical path;

a prism placed in the path of said beam at an angle which permits transmittance of said beam through said prism, said prism having an index of refraction similar to said optical sample;

a layer of index matching fluid on said prism such that while said beam is being transmitted through said prism it encounters said layer and continues on without internal reflection at the boundary of said prism and fluid layer, said optical sample is placed on said fluid layer such that said beam is transmitted into said optical sample without reflection at the boundary of said optical sample and fluid layer and is incident on the opposite side of said optical sample at the critical angle for total internal reflection, said beam interfacing with itself after reflection so as to create a standing wave pattern which scatters light off of imperfections smaller than the wavelength of said standing waves except when said imperfections are located at null points of said standing waves; and means for observing the surface of said optical sample above the area where total internal reflection occurs to observe said scattered light which has been scattered toward said upper surface at less than the critical angle said observation means observing light emitted normal to said optical sample.

5. An apparatus for locating defects in or on an optical sample as described in claim 4 wherein said source of polarized light is comprised of a tunable laser.

6. An apparatus for locating defects in or on an optical sample as described in claim 4 wherein said observing means is a microscope.

7. An apparatus for locating defects in or on an optical sample as described in any of claims 4, 5, or 6 further comprising means for altering the path of said beam in said optical sample such that it is reflected at angles greater than the critical angle.

8. An apparatus for locating defects in or on an optical sample comprising:

a tunable laser for emitting a beam of polarized light along a predetermined path;

a prism placed in the path of said beam at an angle which permits transmittance of said beam through said prism, said prism having an index of refraction similar to said optical sample;

a layer of index matching fluid on said prism such that while said beam is being transmitted through said prism it encounters said layer and continues on without internal reflection at the boundary of said prism and fluid layer, said optical sample is placed on said fluid layer such that said beam is transmitted into said optical sample without reflection at the boundary of said optical sample and fluid layer and is incident on the opposite side of said optical sample at the critical angle for total internal reflection, said beam interfacing with itself after reflection so as to create a standing wave pattern;

a microscope for observing the surface of said optical sample above the area where total internal reflection occurs;

a coating on the surface of said optical sample to remove surface irregularities so that only imbedded imperfections are observed; and means for altering the path of said beam in said optical sample such that it is reflected at angles greater than the critical angle.

9. An apparatus for locating microbes in a coating on an optical sample where the coating and optical sample have matching indexes of refraction comprising:
a tunable laser for emitting a beam of polarized monochromatic light along a predetermined path, said polarization capable of being changed;
a prism placed in the path of said beam at an angle which permits transmittance of said beam through said prism, said prism having an index of refraction similar to said optical sample;
a layer of index matching fluid on said prism such that while said beam is being transmitted through said prism it encounters said layer and continues on without internal reflection at the boundary of said prism and fluid layer, said optical sample is placed on said fluid layer such that said beam is transmitted into said optical sample without reflection at the boundary of said optical sample and fluid layer and is incident on the opposite side of said optical sample at the critical angle for total internal reflection, said beam interfaces with itself after reflection so as to create a standing wave pattern which scatters light off of imperfections smaller than the wavelength of said standing waves except when said imperfections are located at null points of said standing waves;
a microscope for observing the coating on said optical sample where total internal reflection occurs said microscope placed to observe light emitted normal to said optical sample; and
means for altering the path of said beam in said optical sample such that it is reflected at angles greater than the critical angle except for scattered light which has been scattered off of imperfections toward said upper surface at less than the critical angle.

10. A surface inspection method for finding defects contained in or on an optical sample comprising the steps of:
coating one side of a prism whose index of refraction is similar to said optical sample with an index matching fluid;
placing said optical sample on said fluid coated side;
covering said optical sample with a coating to remove all surface irregularities such that the only imperfections viewed at said observation point are those imbedded within said optical sample;
establishing an observation point above said optical sample;
directing a beam of polarized light into said prism such that said beam reflects off of the upper surface of said optical sample at the critical angle beneath said observation point so as to create a standing wave pattern; and
moving said optical sample so that all areas of said optical sample are viewed from said observation point.

11. A surface inspection method for finding defects contained in or on an optical sample as described in claim 10 further comprising the step of:
varying the characteristic wavelength of said polarized light such that the standing wave patterns within said optical sample vary the locations of peaks and nulls to locate the position of imperfections within said optical sample.

12. A surface inspection method for finding defects contained in or on an optical sample as described in claim 10 further comprising the step of:
changing the polarization of said polarized light such that the standing wave patterns within said optical sample vary the locations of peaks and nulls to locate the position of imperfections within said optical sample.

13. A surface inspection method for finding defects contained in or on an optical sample as described in claim 11 further comprising the step of:
changing the polarization of said polarized light such that the standing wave patterns within said optical sample vary the locations of peaks and nulls to locate the position of imperfections within said optical sample.

14. A surface inspection method for finding defects contained in or on an optical sample as described in either of claims 10, 11, 12, or 13 further comprising the step of:
altering the incident angle of said beam of polarized light to one greater than the critical angle such that the standing wave pattern expands to show imbedded imperfections at different depths in said optical sample.

15. An apparatus for locating defects in or on an optical sample comprising:
a source of polarized light for emitting a beam of light along an optical path;
a prism placed in the path of said beam at an angle which permits transmittance of said beam through said prism, said prism having an index of refraction similar to said optical sample;
a layer of index matching fluid on said prism such that while said beam is being transmitted through said prism it encounters said layer and continues on without internal reflection at the boundary of said prism and fluid layer, said optical sample is placed on said fluid layer such that said beam is transmitted into said optical sample without reflection at the boundary of said optical sample and fluid layer and is incident on the opposite side of said optical sample at the critical angle for total internal reflection, said beam interfacing with itself after reflection so as to create a standing wave pattern;
a coating on the surface of said optical sample to remove surface irregularities so that only imbedded imperfections are observed; and
means for observing the surface of said optical sample above the area where total internal reflection occurs.

16. An apparatus for locating defects in or on an optical sample as described in claim 15 wherein said source of polarized light is comprised of a tunable laser.

17. An apparatus for locating defects in or on an optical sample as described in either claim 15 or 16 wherein said observing means is a microscope.

* * * * *